(12) United States Patent
Kyoda et al.

(10) Patent No.: US 7,772,440 B2
(45) Date of Patent: Aug. 10, 2010

(54) PROCESS FOR PREPARING PHOSPONATES HAVING ALCOHOLIC HYDROXYL GROUP

(75) Inventors: Makoto Kyoda, Aichi (JP); Manabu Hirata, Aichi (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 359 days.

(21) Appl. No.: 11/718,268

(22) PCT Filed: Oct. 18, 2005

(86) PCT No.: PCT/JP2005/019131

§ 371 (c)(1), (2), (4) Date: Apr. 30, 2007

(87) PCT Pub. No.: WO2006/049010

PCT Pub. Date: May 11, 2006

(65) Prior Publication Data

US 2009/0062568 A1    Mar. 5, 2009

(30) Foreign Application Priority Data

Nov. 2, 2004  (JP) .............................. 2004-319528

(51) Int. Cl.
    *G07F 9/02*  (2006.01)
(52) U.S. Cl. ........................................ 568/15
(58) Field of Classification Search ........................ None
    See application file for complete search history.

(56) References Cited

U.S. PATENT DOCUMENTS 5,917,074 A * 6/1999 Hammond et al. .......... 556/404

FOREIGN PATENT DOCUMENTS

| GB | 682706 | 11/1950 |
|---|---|---|
| JP | 46-021933 | 6/1971 |
| JP | 49-126623 | 4/1974 |
| JP | 07-324092 | * 12/1995 |

OTHER PUBLICATIONS

Yan et al., {Design and synthesis of conformationally constrained 3-(N-alkylamino)propylphosphonic acids as potent agonists of sphingosine-1-phosphate (S1P) receptors, Bioorganic & Medicinal Chemistry Letters (2004), 14(19), 4861-4866}.*
Benayoud et al., {Efficient Syntheses of (a-Fluoropropargyl)phosphonate Esters, Journal of Organic Chemistry (1996), 61(15), 5159-5164}.*
Duxbury et al., {Phospho-Aldol Catalysis via Chiral Schiff Base Complexes of Aluminum, Organometallics (2000), 19(22), 4445-4457}.*
S. Kumaraswamy et al.; Synthesis, 1997, No. 2, pp. 207-212.
D. Simoni et al.; Tetrahedron Letters, 1998, vol. 39, No. 41, pp. 7615-7618.
D. Simoni et al.; Tetrahedron Letters, 2000, vol. 41, No. 10, pp. 1607-1610.
S. Sebti et al.; Tetrahedron Letters, 1996, vol. 37, No. 23, pp. 3999-4000.
U.S. Appl. No. 11/718,296, filed Apr. 30, 2007, and entitled "Process for preparing compounds having phosphate-phosphonate bond".
English language Abstract of JP 07-324092.
D. Simoni et al.; Tetrahedron Letters, 2002, vol. 43, No. 46, pp. 8323-8325.
D. Simoni et al.; Tetrahedron Letters, 2003, vol. 44, No. 3, pp. 587-589.
D. Simoni et al.; Tetrahedron Letters, 1987, vol. 28, No. 36, pp. 4135-4138.
Journal of Organic Chemistry, 1992, vol. 57, No. 10, pp. 2937-2941.

* cited by examiner

*Primary Examiner*—Porfirio Nazario Gonzalez
*Assistant Examiner*—Chukwuma O Nwaonicha
(74) *Attorney, Agent, or Firm*—Greenblum & Bernstein, P.L.C.

(57) ABSTRACT

A novel process for preparing in a high purity and in a high yield phosphonates having a secondary and/or tertiary alcoholic hydroxyl group at the end of a P—C bond chain thereof with the use of a phosphite and a carbonyl compound as raw materials.

7 Claims, No Drawings

PROCESS FOR PREPARING PHOSPONATES HAVING ALCOHOLIC HYDROXYL GROUP

TECHNICAL FIELD

The present invention relates to a novel process for preparing a phosphonate having a secondary and/or tertiary alcoholic hydroxyl group in a high purity and in a high yield.

BACKGROUND ART

As an intermediate raw material or the like in the chemical industry, phosphonates having an alcoholic hydroxyl group have various applications. For example, as an intermediate in synthesis for preparing phosphoric esters that are known generally as a flame-retarder for resins, the phosphonates are used for preparing the phosphoric esters by being reacted with a compound having a P—Cl bond.

As a process for preparing such phosphonates, various processes are known.

For example, Japanese Unexamined Patent Publication No. Sho 49 (1974)-126623 describes a process for synthesizing phosphonates having an alcoholic hydroxyl group by reacting a dialkyl phosphite with a carbonyl compound in the presence of a catalyst of an amine compound such as triethylamine or tributylamine and a metal alkoxide such as sodium ethoxide.

With this process, however, the target compound cannot be obtained in a high yield, and unreacted raw materials are left in the reaction product. Further, improving the purity of the target compound requires a step for removing the unreacted raw materials, which leads to a reduced yield and an increased amount of a by-product due to thermal history applied at the removal step.

Also, the specification of British Patent No. 682706 describes a process for synthesizing phosphonates having an alcoholic hydroxyl group by reacting a dialkyl phosphite with a carbonyl compound in the presence of a catalyst of an alkali metal such as metallic potassium or metallic sodium.

The alkali metal used in this process as the catalyst, however, poses a danger in handling during storage or use, and therefore the use of the alkali metal is not preferable in industry. Further, the yields of the target compounds mentioned in the Examples of this patent document are not satisfactory.

Generally, if carbonyl compounds used as a raw material are an aldehyde or a ketone having a sterically bulky substituent, the carbonyl compounds are prone to be inferior in reactivity. For this reason, there has been a demand for development of a process for preparing phosphonates in a high yield even with the use of such a carbonyl compound having a sterically bulky substituent as a raw material.

DISCLOSURE OF INVENTION

It is an object of the present invention to provide a novel process for preparing in a high purity and in a high yield phosphonates having a secondary and/or tertiary alcoholic hydroxyl group at the end of a P—C bond chain thereof with the use of a phosphite and a carbonyl compound as raw materials.

The present inventors, as a result of eager studies to solve the above problem, have found that, by subjecting a phosphite having two substituents and a carbonyl compound to an addition reaction in the coexistence of a nitrogen-containing basic compound and a metallic halide, a phosphonate having an alcoholic hydroxyl group can be prepared in a high purity and in a high yield, along with only an extremely small amount of a by-product, to complete the present invention.

Thus, the present invention provides a process for preparing a phosphonate, comprising the steps of: subjecting a phosphite represented by the general formula (II):

wherein $R^1$ and $R^2$ are, the same as or different from each other, a straight or branched alkyl, cycloalkyl or aryl group; or alternatively $R^1$ and $R^2$, together with the oxygen atom and phosphorus atom to which they are attached, may constitute a ring structure and a carbonyl compound represented by the general formula (III):

wherein $R^3$ and $R^4$ are, the same as or different from each other, a hydrogen atom or a straight or branched alkyl or aryl group; or alternatively $R^3$ and $R^4$, together with the carbon atom to which they are attached, may constitute a ring structure, but $R^3$ and $R^4$ are not a hydrogen atom at the same time to an addition reaction in the coexistence of a nitrogen-containing basic compound and a metallic halide, to obtain a phosphonate having a secondary and/or tertiary alcoholic hydroxyl group represented by the general formula (I):

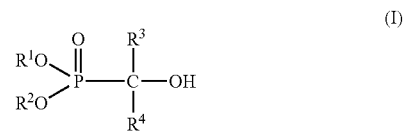

wherein $R^1$, $R^2$, $R^3$ and $R^4$ each are as defined above.

According to the present invention, phosphonates having a secondary and/or tertiary alcoholic hydroxyl group at the end of a P—C bond chain thereof can be prepared in a high purity and in a high yield with the use of a phosphite (II) and a carbonyl compound (III) as raw materials.

BEST MODE FOR CARRYING OUT THE INVENTION

The process for preparing a phosphonate according to the present invention comprises subjecting a phosphite (II) and a carbonyl compound (III) to an addition reaction in the coexistence of a nitrogen-containing basic compound and a metallic halide, to obtain a phosphonate (I) having a secondary and/or tertiary alcoholic hydroxyl group.

$R^1$ and $R^2$ in the phosphite (II) may be, the same as or different from each other, a straight or branched alkyl, cycloalkyl or aryl group. Or alternatively $R^1$ and $R^2$, together with the oxygen atom and phosphorus atom to which they are attached, may constitute a ring structure.

Examples of the straight or branched alkyl groups for $R^1$ and $R^2$ include methyl, ethyl, n-propyl, iso-propyl, n-butyl, iso-butyl, sec-butyl, n-pentyl, n-hexyl, n-octyl and 2-ethylhexyl, among which particularly preferable are $C_2$-$C_8$ alkyl groups.

It is not preferable that at least one of $R^1$ and $R^2$ is a methyl group because in such a case, the phosphonate (II) and the phosphonate (I) are easy to decompose, and a low yield of the phosphonate (I) may be resulted. Also, it is not preferable that at least one of $R^1$ and $R^2$ is an alkyl group having 9 or more carbon atoms, because in such a case, an alcohol having a large number of carbon atoms that generates from preparation of the phosphite (II) may be left in the final product and difficult to remove.

Examples of the cycloalkyl groups for $R^1$ and $R^2$ include cyclopropyl, cyclobutyl, cyclopentyl, cyclohexyl, cycloheptyl, cyclooctyl, cyclononyl and cyclodecyl, among which preferable are $C_5$-$C_7$ cycloalkyl groups and particularly preferable is a cyclohexyl group.

A cycloalkyl group having a ring structure constituted of 8 or more carbon atoms and a cycloalkyl group having a ring structure constituted of 4 or less carbon atoms are not preferable, because the cycloalkyl ring is prone to be unstable, and as a result, a by-product resulting from cleavage of the ring may give adverse effects to the reaction system.

The cycloalkyl group for $R^1$ and $R^2$ may have a substituent. Examples of the substituents include $C_1$-$C_5$ straight and branched alkyl groups, among which particularly preferable are, for example, $C_1$-$C_4$ alkyl groups such as methyl, ethyl, n-propyl, n-butyl, iso-butyl, sec-butyl and tert-butyl.

Examples of the cycloalkyl groups having a substituent include a 3-methylcyclohexyl group and a 4-methylcyclohexyl group. It is preferable that the phosphite (II) has such a group, because in such a case, the phosphite (II) is readily available as a raw material and because an alcohol that generates from the preparation of the phosphite (II) is easy to remove from the final product.

Examples of the aryl groups for $R^1$ and $R^2$ include phenyl, 1-naphtyl and 2-naphtyl.

The aryl group for $R^1$ and $R^2$ may have a substituent. Examples of the substituents include $C_1$-$C_9$ straight and branched alkyl groups, among which particularly preferable are, for example, $C_1$-$C_4$ alkyl groups such as methyl, ethyl, n-propyl, n-butyl, iso-butyl, sec-butyl and tert-butyl.

Examples of the aryl groups having a substituent include $C_6$-$C_{15}$ aryl groups such as 2-methylphenyl, 3-methylphenyl, 4-methylphenyl, 2,6-dimethylphenyl, 2,4-dimethylphenyl, 3,5-dimethylphenyl and 2,6-di-tert-butyl-4-methylphenyl.

It is preferable that the phosphite (II) has a phenyl group, a 3-methylphenyl group or a 4-methylphenyl group among the above aryl groups, because in such a case, the phosphite (II) is readily available as a raw material, and a phenol that generates from preparation of the phosphite (II) are easy to remove from the final product.

Or alternatively, $R^1$ and $R^2$, together with the oxygen atom and phosphorus atom to which they are attached, may constitute a ring structure. The substituent —$R^1$—$R^2$— consisting of $R^1$ and $R^2$ in bond is preferably an alkylene group in which the sum of the numbers of carbon atoms contained in $R^1$ and $R^2$ is 2 to 9, and more preferably an alkylene group in which the sum is 2 to 6. The ring in the ring structure is preferably a five- to seven-membered ring, more preferably a five-membered ring or a six-membered ring, and particularly preferably a six-membered ring. Eight- and more-membered rings and four- and less-membered rings are not preferable, because these rings are prone to be unstable, with the result that an acidic constituent [P—OH] produced due to cleavage of the ring may give adverse effects to progress of the reaction.

Examples of the particularly preferable ring structures include a ring structure represented by the following general formula (IV):

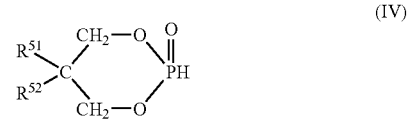

(IV)

wherein $R^{51}$ and $R^{52}$ are, the same as or different from each other, a hydrogen atom or a straight or branched alkyl group.

It is preferable that $R^{51}$ and $R^{52}$ are such that the sum of the numbers of carbon atoms contained in $R^{51}$ and $R^{52}$ is 0 to 6. Specifically mentioned are a combination of a methyl group and a methyl group as $R^{51}$ and $R^{52}$, respectively, and a combination of an ethyl group and an n-butyl group as $R^{51}$ and $R^{52}$, respectively, and the like combination.

The phosphite (II) as mentioned above is preferably a dialkyl phosphite in which two alkyl groups for $R^1$ and $R^2$, respectively, are the same, a diaryl phosphite or a cyclic phosphite in terms of ease of acquisition as a raw material and in terms of cost. For example, dialkyl phosphites such as a diethyl phosphite, di-n-propylphosphite, di-n-butylphosphite, di-n-octylphosphite and bis(2-ethylhexyl)phosphite; diaryl phosphites such as diphenylphosphite; and a cyclic phosphite such as neopentylene phosphite may be mentioned. Among these, particularly preferable are di-n-butylphosphite, bis(2-ethylhexyl)phosphite and neopentylene phosphite.

$R^3$ and $R^4$ in the carbonyl compound (III) may be, the same as or different from each other, a hydrogen atom or a straight or branched alkyl or aryl group. Or alternatively $R^3$ and $R^4$, together with the carbon atom to which they are attached, may constitute a ring structure, but $R^3$ and $R^4$ are not a hydrogen atom at the same time.

Examples of the straight or branched alkyl groups for $R^3$ and $R^4$ include methyl, ethyl, n-propyl, iso-propyl, n-butyl, iso-butyl, sec-butyl, n-pentyl and n-hexyl, among which particularly preferable are $C_1$-$C_6$ alkyl groups.

Examples of the aryl groups for $R^3$ and $R^4$ include a phenyl group.

The aryl group for $R^3$ and $R^4$ may have a substituent. Examples of the substituents include $C_1$-$C_7$ straight and branched alkyl groups, among which particularly preferable are, for example, $C_1$-$C_4$ alkyl groups such as methyl, ethyl, n-propyl, n-butyl, iso-butyl, sec-butyl and tert-butyl.

Examples of the aryl groups having a substituent include 2-methylphenyl, 3-methylphenyl, 4-methylphenyl, 2,6-dimethylphenyl, 2,4-dimethylphenyl and 3,5-dimethylphenyl.

Or alternatively $R^3$ and $R^4$, together with the carbon atom to which they are attached, may constitute a ring structure represented by the following formula:

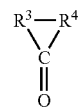

The substituent —$R^3$—$R^4$— consisting of $R^3$ and $R^4$ in bond is preferably an alkylene group in which the sum of the numbers of carbon atoms contained in $R^3$ and $R^4$ is 4 to 10. The ring in the ring structure is preferably a five- to seven-membered ring, and particularly preferably a six-membered ring.

The carbonyl compound (III) is preferably such that $R^3$ is a hydrogen atom and the number of carbon atoms contained in $R^4$ is 1 to 10.

Such a carbonyl compound (III) may be acetaldehyde, propionaldehyde, butyraldehyde or benzaldehyde.

Also, the carbonyl compound (III) is preferably such that the numbers of carbon atoms contained in $R^3$ and $R^4$ each are 1 or more and that the sum of the number of carbon atoms contained in $R^3$ and $R^4$ is 2 to 12.

Such a carbonyl compound (III) may be acetone, methyl ethyl ketone, methyl iso-butyl ketone, cyclohexanone, acetophenone or benzophenone.

If $R^3$ and $R^4$ have a substituent as mentioned above, or if $R^3$ and $R^4$, together with the carbon atom to which they are attached, may constitute a ring structure, the carbonyl compound (III) has a sterically bulky substituent, and as a result, it is expected that its reactivity with the phosphite (II) will be low. However, according to the preparation process of the present invention, the reaction proceeds smoothly contrary to the expectation.

Next, there will be explained in detail the reaction of the phosphite (II) and the carbonyl compound (III) according to the present invention.

The preparation process of the present invention comprises the step of subjecting a phosphite (II) and a carbonyl compound (III) to an addition reaction in the coexistence of a nitrogen-containing basic compound and a metallic halide.

In the preparation process of the present invention, the use of the nitrogen-containing basic compound and the metallic halide in combination is a requisite, and with the single use of either one of them, the reaction does not proceed smoothly.

Examples of the nitrogen-containing basic compounds used in the preparation process according to the present invention include metallic amides such as lithium amide and sodium amide; cyclic amines such as 1,8-diazabicyclo(5,4,0)undecene-7 (DBU) and 1,4-diazabicyclo(2,2,2)octane; aliphatic tertiary amines such as trimethylamine, diethylamine, triethylamine and tributylamine; heterocyclic amines such as 4-dimethylaminopyridine, pyridine, lutidine and picoline. These nitrogen-containing basic compounds may be used in a combination of two or more.

Among these nitrogen-containing basic compounds, preferable are sodium amide, triethylamine and DBU in terms of capability to selectively prepare the phosphonate (I), and particularly preferable is triethylamine in terms of ease of acquisition as a raw material and in terms of ease of handling.

It is preferable that the nitrogen-containing basic compound is used preferably in 1 to 50 mol %, and more preferably in 3 to 20 mol % with respect to the phosphite (II).

It is not preferable that the nitrogen-containing basic compound is used in less than 1 mol % with respect to the phosphite (II) because in such a case, the yield of the phosphonate (I) will decline. Also, it is not preferable either that the nitrogen-containing basic compound is used in more than 50 mol % with respect to the phosphite (II) because no further improvement in the yield of the phosphonate (I) can be expected.

Examples of the metallic halides used in the preparation process according to the present invention include as magnesium chloride, aluminum chloride, zinc chloride, titanium tetrachloride and a boron trifluoride ether complex, among which particularly preferable is magnesium chloride. The above metallic halides may be used in a combination of two or more.

The metallic halide is preferably used in 0.1 to 5 mol % and particularly preferably in 1 to 4 mol % with respect to the phosphite (II), and may be used in an amount properly set according to the reactivity of the phosphite (II) and the carbonyl compound (III).

It is not preferable that the metallic halide is used in less than 0.1 mol % with respect to the phosphite (II) because in such a case, the yield of the phosphonate (I) will decline. Also, it is not preferable either that the metallic halide is used in more than 5 mol % with respect to the phosphite (II) because no further improvement in the yield of the phosphonate (I) can be expected and because the phosphonate (I) may decompose.

A particularly preferable combination of the nitrogen-containing basic compound and the metallic halide may be a combination of triethylamine and magnesium chloride.

According to the preparation process of the present invention, the phosphite (II) and the carbonyl compound (III) are used in a ratio of the carbonyl compound (III) to the phosphite (II) of 1.0 to 1.5 mol %, and preferably of 1.0 to 1.2 mol %.

It is not preferable that the ratio of the carbonyl compound (III) to the phosphite (II) is less than 1.0 mol % because in such a case, the phosphite (II) will be left in a large amount in the reaction mixture, resulting in a low rate of conversion into the phosphonate (I) (yield of the target compound). Also, though unreacted carbonyl compound (III) left in the reaction mixture when excess carbonyl compound (III) is used can be readily removed by, for example, removing the low-boiling point portions under a reduced pressure, it is not preferable that 1.5 mole of the carbonyl compound (III) is used with respect to 1 mole of the phosphite (II) because in such a case, there will be a large amount of unreacted carbonyl compound (III) to be removed.

The reaction temperature in the above addition reaction is preferably 10 to 100° C. and more preferably 20 to 70° C. It is not preferable that the reaction temperature is below 10° C. because in such a case, the reactivity is low. Also, it is not preferable that the reaction temperature exceeds 100° C. because in such a case, the carbonyl compound (III) and the nitrogen-containing basic compound will release or because a secondary reaction such as decomposition will proceed.

Also, usually, about 1 to 5 hours is sufficient for the reaction time though the reaction time depends on conditions such as the reaction temperature.

The above addition reaction can be carried out in the presence of an organic solvent as required.

The solvent is not particularly limited as long as it is a solvent inert to this reaction, and examples of the solvents include hydrocarbon solvents such as pentane, hexane, benzene, toluene and xylene; halogen-containing hydrocarbon solvents such as monochlorobenzene, dichlorobenzene, 1,2-dichloroethane; and ether solvents such as diethyl ether and 1,4-dioxane.

By removing under reduced pressure the solvent and the low-boiling point components from the reaction mixture obtained, the phosphorus compound of the general formula (I) can be obtained which is the target compound.

Also, if it is intended to avoid metallic components and acidic components, which are derived from the nitrogen-containing basic compound and the metallic halide used as the catalysts and from the solvent and the like, from being left in the reaction mixture, they are preferably removed by a known method. Examples of removal methods include acid washing, alkali washing, rinsing with water and vacuum distillation.

With acid washing, the metallic components derived from the metallic halide of the reaction mixture, and the nitrogen-containing basic compound can be removed. Specifically, the reaction mixture obtained is washed with acidic water such as hydrochloric acid, sulfuric acid, oxalic acid, nitric acid, phosphoric acid or citric acid.

With alkali washing, the acidic components can be removed from the reaction mixture through neutralization. Specifically, the reaction mixture obtained is washed with an alkaline aqueous solution such as sodium hydroxide, potassium hydroxide or sodium carbonate.

As an intermediate raw material or the like in the chemical industry, the phosphonate according to the present invention has various applications. For example, the phosphonate according to the present invention can be used as an intermediate that derives a phosphoric ester known generally as a flame-retarder for resins.

Specifically, the phosphonate according to the present invention and a compound having a P—Cl bond such as a disubstituted phosphorus halidate are subjected to a dehydrohalogenation reaction, and then the resulting reaction product is oxidized, to obtain an organic phosphorus compound having a phosphate-phosphonate bond within one molecule.

In the above, the present invention has been explained by way of preferable examples. However, the present invention should not be construed as being limited to these examples. A skilled person in the art can carry out the present invention by applying equivalent ranges derived from the descriptions of preferable examples of the present application while referring to the descriptions of the present application and to common general technical knowledge. The disclosures of the documents cited in the present specification are incorporated by reference in its entirety, as is the case with the descriptions of the documents specifically contained therein.

EXAMPLES

The present invention will be explained in detail by way of the following examples and comparative examples, which should not be construed to limit the scope of the invention.

Example 1

Into a two-liter four-necked flask provided with a stirrer, a thermometer, a dropping device and a condenser, 194.0 g (1 mol) of dibutyl phosphite, 5.1 g (0.05 moles) of triethylamine and 1.7 g (0.018 moles) of magnesium chloride were fed. While stirring the mixed solution at 40° C., 63.8 g (1.1 moles) of acetone was added thereto in 1 hour. The mixture was further stirred at the same temperature (40° C.) for 1 hour to obtain 264.6 g of a reaction solution containing dibutyl(1-hydroxy-1-methylethyl)phosphonate as a main component.

The reaction solution obtained was measured by gel permeation chromatography (GPC) and the reaction ratio (area percentage) of the main component was determined by calculation, and the reaction ratio was found to be 99.7%.

Table 1 shows the results obtained, along with raw materials and catalysts used, amounts thereof, and reaction conditions.

Thereafter, the dibutyl(1-hydroxy-1-methylethyl)phosphonate obtained was subjected to purification as follows. First, the reaction solution was heated to 60° C., washed with a 2% dilute hydrochloric acid aqueous solution to remove triethylamine and magnesium chloride from the reaction solution. Next, the reaction solution was washed with a saturated sodium carbonate aqueous solution and further rinsed with water twice to remove acidic components from the reaction solution. Then, while heating the reaction solution to 80° C., water was restored under a reduced pressure of about 2.7 kPa. Further, nitrogen topping was carried out under the same conditions to remove unreacted raw materials, thereby obtaining 242.2 g of dibutyl(1-hydroxy-1-methylethyl)phosphonate. The purity was measured by GPC, and it was found to be 99.8%.

Example 2

Into a two-liter four-necked flask provided with a stirrer, a thermometer, a dropping device and a condenser, 194.0 g (1 mole) of dibutyl phosphite, 5.1 g (0.05 moles) of triethylamine and 0.95 g (0.01 moles) of magnesium chloride were fed. While stirring the mixed solution at 25° C., 110.0 g (1.1 moles) of methyl isobutyl ketone (MIBK) was added thereto in 1 hour. The mixture was further stirred at the same temperature (25° C.) for 1 hour to obtain 310.1 g of a reaction solution containing dibutyl(1-hydroxy-1,3-dimethylbutyl)phosphonate as a main component.

The reaction solution obtained was measured by GPC and the reaction ratio (area percentage) of the main component was determined by calculation, and the reaction ratio was found to be 96.4%.

Table 1 shows the results obtained, along with raw materials and catalysts used, amounts thereof, and reaction conditions.

Example 3

A reaction solution of 308.6 g containing dibutyl(1-hydroxy-cyclohexyl)phosphonate as a main component was obtained in the same manner as in Example 1 except that 107.8 g (1.1 moles) of cyclohexanone was used instead of acetone and that the temperature was set at 60° C.

The reaction solution obtained was measured by GPC and the reaction ratio (area percentage) of the main component was determined by calculation, and the reaction ratio was found to be 99.8%.

Table 1 shows the results obtained, along with raw materials and catalysts used, amounts thereof, and reaction conditions.

Example 4

A reaction solution of 393.4 g containing bis(2-ethylhexyl)(1-hydroxy-1-methylethyl)phosphonate as a main component was obtained in the same manner as in Example 1 except that 306.0 g (1 mole) of bis(2-ethylhexyl)phosphite was used instead of dibutylphosphite and that 20.2 g (0.2 moles) of triethylamine and 3.4 g (0.036 moles) of magnesium chloride were used.

The reaction solution obtained was measured by GPC and the reaction ratio (area percentage) of the main component was determined by calculation, and the reaction ratio was found to be was 100.0%.

Table 1 shows the results obtained, along with raw materials and catalysts used, amounts thereof, and reaction conditions.

Example 5

A reaction solution of 468.5 g containing neopentylene(1-hydroxy-1-methylethyl)phosphonate as a main component was obtained in the same manner as in Example 1 except that 150.0 g (1 mole) of neopentylene phosphite was used instead of dibutylphosphite, that 3.0 g (0.03 moles) of triethylamine and 1.7 g (0.018 moles) of magnesium chloride were used, and that 250 g of chlorobenzene was used as a solvent.

The reaction solution obtained was measured by GPC and the reaction ratio (area percentage) of the main component was determined by calculation, and the reaction ratio was found to be 99.0%.

Table 1 shows the results obtained, along with raw materials and catalysts used, amounts thereof, and reaction conditions.

Example 6

A reaction solution of 263.4 g containing dibutyl(1-hydroxy-1-methylethyl)phosphonate as a main component was obtained in the same manner as in Example 1 except that 3.9 g (0.1 moles) of sodium amide was used instead of triethylamine.

The reaction solution obtained was measured by GPC and the reaction ratio (area percentage) of the main component was determined by calculation, and the reaction ratio was found to be 96.2%.

Table 1 shows the results obtained, along with raw materials and catalysts used, amounts thereof, and reaction conditions.

Comparative Example 1

A transparent and colorless reaction solution was obtained in the same manner as in Example 1 except that magnesium chloride was not used.

The reaction solution obtained was measured by GPC and the reaction ratio (area percentage) of the main component was determined by calculation, and the reaction ratio was found to be 7.5%.

Table 2 shows the results obtained, along with raw materials and catalysts used, amounts thereof, and reaction conditions.

Comparative Example 2

The reaction was attempted in the same manner as in Example 1 except that triethylamine was not used. GPC analysis indicated that no target product was prepared, and it was judged that no reaction occurred.

Table 2 shows the results obtained, along with raw materials and catalysts used, amounts thereof, and reaction conditions.

Comparative Example 3

A transparent and colorless reaction solution of 263.2 g was obtained in the same manner as in Example 1 except that 5.4 g (0.1 moles) of sodium methoxide was used instead of both triethylamine and magnesium chloride.

The reaction solution obtained was measured by GPC and the reaction ratio (area percentage) of the main component was determined by calculation, and the reaction ratio was found to be 11.3%.

Table 2 shows the results obtained, along with raw materials and catalysts used, amounts thereof, and reaction conditions.

Comparative Example 4

A transparent and colorless reaction solution of 261.7 g was obtained in the same manner as in Example 6 except that magnesium chloride was not used.

The reaction solution obtained was measured by GPC and the reaction ratio (area percentage) of the main component was determined by calculation, and the reaction ratio was found to be 27.2%.

Table 2 shows the results obtained, along with raw materials and catalysts used, amounts thereof, and reaction conditions.

TABLE 1

|  | Example 1 | Example 2 | Example 3 | Example 4 | Example 5 | Example 6 |
|---|---|---|---|---|---|---|
| Phosphite (II) | Dibutyl phosphite (1 mole) | Dibutyl phosphite (1 mole) | Dibutyl phosphite (1 mole) | Bis(2-ethylhexyl) phosphite (1 mole) | Neopentylene phosphite (1 mole) | Dibutyl phosphite (1 mole) |
| Organic carbonyl compound (III) | Acetone (1.1 moles) | Methyl isobutyl ketone (1.1 moles) | Cyclohexanone (1.1 moles) | Acetone (1.1 moles) | Acetone (1.1 moles) | Acetone (1.1 moles) |
| Nitrogen-containing basic compound | Triethylamine (0.05 moles) | Triethylamine (0.05 moles) | Triethylamine (0.05 moles) | Triethylamine (0.2 moles) | Triethylamine (0.03 moles) | Sodium amide (0.1 moles) |
| Metallic halide | Magnesium chloride (0.018 moles) | Magnesium chloride (0.01 moles) | Magnesium chloride (0.018 moles) | Magnesium chloride (0.036 moles) | Magnesium chloride (0.018 moles) | Magnesium chloride (0.018 moles) |
| Reaction temperature (° C.) | 40 | 25 | 60 | 40 | 40 | 40 |
| Reaction time (hr) | 2 | 2 | 2 | 2 | 2 | 2 |
| Reaction ratio (%) | 99.7 | 96.4 | 99.8 | 100.0 | 99.0 | 96.2 |

TABLE 2

|  | Comparative Example 1 | Comparative Example 2 | Comparative Example 3 | Comparative Example 4 |
|---|---|---|---|---|
| Phosphite (II) | Dibutyl phosphite (1 mole) | Dibutyl phosphite (1 mole) | Dibutyl phosphite (1 mole) | Dibutyl phosphite (1 mole) |
| Organic carbonyl compound (III) | Acetone (1.1 moles) | Acetone (1.1 moles) | Acetone (1.1 moles) | Acetone (1.1 moles) |
| Nitrogen-containing | Triethylamine (0.05 moles) | — | —* | Sodium amide |

TABLE 2-continued

| | Comparative Example 1 | Comparative Example 2 | Comparative Example 3 | Comparative Example 4 |
|---|---|---|---|---|
| basic compound | | | | (0.1 moles) |
| Metallic halide | — | Magnesium chloride (0.018 moles) | —* | — |
| Reaction temperature (° C.) | 40 | 40 | 40 | 40 |
| Reaction time (hr) | 2 | 2 | 2 | 2 |
| Reaction ratio (%) | 7.5 | No reaction | 11.3 | 27.2 |

*5.4 g (0.1 moles) of sodium methoxide was used.

From the results of Table 1, it is understood that, in Examples 1 to 6, in which a phosphite having two substituents and a carbonyl compound were subjected to the addition reaction in the coexistence of a nitrogen-containing basic compound and a metallic halide, a phosphonate was obtained in a high yield. Especially, it is understood that, in Example 2 in which the sterically bulky methyl iso-butyl ketone, the reactivity of which is expected to be still lower than that of the acetone of Example 1, was used as the carbonyl compound, its reactivity was favorable.

On the other hand, from the results of Table 2, it is understood that in Comparative Example 1 in which only the triethylamine was used as the nitrogen-containing basic compound; in Comparative Example 2 in which only the magnesium chloride was used as the metallic halide; in Comparative Example 3 in which none of the nitrogen-containing basic compound and the metallic halide was used; and in Comparative Example 4 in which only the sodium amide was used as, the nitrogen-containing basic compound, the reaction hardly proceeded. This indicates that the reaction does not proceed smoothly as long as the nitrogen-containing basic compound and the metallic halide are not used in combination.

Reference Example 1

Dibutyl(1-hydroxy-1-methylethyl)phosphonate of 242.2 g was obtained in the same manner as in Example 1.

(Step (1))

After completion of the above reaction, 142.0 g of toluene and 111.1 g (1.10 moles) of triethylamine were fed into a two-liter four-necked flask containing dibutyl(1'-hydroxy-1-methylethyl)phosphonate, and the resulting mixed solution was stirred. Next, while maintaining the mixed solution at 60° C. in a thermostat, 182.0 g (1.08 moles) of neopentylenephosphorus chloridate was added thereto in 2 hours from a dropping device (funnel). Thereafter, the reaction mixture was stirred at the same temperature (60° C.) for 1 hour to complete the reaction.

Water of 200 g (about 30 wt % with respect to the reaction mixture) was added to the reaction mixture. The resulting solution was stirred at the same temperature (60° C.) for 30 min. and then allowed to stand to be separated into phases. The aqueous phase was recovered to remove triethylamine hydrochloride prepared as a by-product.

(Step (2))

Subsequently, the reaction solution obtained was cooled to 20° C., and 3.0 g (0.03 moles) of triethylamine was added thereto so that the mixed solution was of pH 10. Then, 104.9 g of a 35% hydrogen peroxide aqueous solution (1.08 moles as hydrogen peroxide) was added in 2 hours from the dropping device (funnel), while paying attention to heat generation in order for the temperature not to go out of the range of 20 to 40° C. Thereafter, the mixture was stirred at 40° C. for 1 hour.

Then, the resulting reaction solution was heated to 60° C., washed with a 1% dilute hydrochloric acid aqueous solution and a saturated sodium carbonate aqueous solution successively and finally rinsed with water twice. Thereafter, while heating the reaction mixture to 100° C., water and toluene were recovered under a reduced pressure of 13.3 kPa. Further, steam topping and nitrogen topping were successively carried out at 100 to 110° C. under a reduced pressure of 2.7 kPa to remove low-boiling point portions, thereby obtaining 374.3 g of a transparent and colorless liquid (phosphate-phosphonate compound).

The purity of the product obtained was measured by a gas chromatograph and the yield thereof was determined by calculation, and they were found to be 98.6% and 96.2%, respectively.

Also, the structure of the product obtained was determined according to IR, NMR, element analysis and absorption analysis based on P %.

IR (KBr):
2976, 1469, 1376, 1306, 1261, 1213, 1149, 1056, 1014, 915, 851, 813, 742, 624 cm$^{-1}$

NMR:
$^1$H-NMR (CDCl$_3$; 400 MHz); δ 4.26 (2H, d, $J_{HH}$=10 Hz, POC$\underline{H}_2$C(CH$_3$)$_2$—), 4.144 (2H, t, $J_{HH}$=7 Hz, POC$\underline{H}_2$CH$_2$CH$_2$CH$_3$), 4.141 (2H, t, $J_{HH}$=7 Hz, POC$\underline{H}_2$CH$_2$CH$_2$CH$_3$), 3.86 (2H, dd, $J_{HH}$=10 Hz, $J_{PH}$=23 Hz, POC$\underline{H}_2$C(CH$_3$)$_2$—), 1.80 (3H, s, PC(C$\underline{H}_3$)$_2$O), 1.76 (3H, s, PC(C$\underline{H}_3$)$_2$O), 1.69 (4H, m, POCH$_2$C$\underline{H}_2$CH$_2$CH$_3$), 1.43 (4H, tq, $J_{HH}$=7 Hz, POCH$_2$CH$_2$C$\underline{H}_2$CH$_3$), 1.29 (3H, s, POCH$_2$C(C$\underline{H}_3$)$_2$—), 0.96 (6H, t, $J_{HH}$=7 Hz, POCH$_2$CH$_2$CH$_2$C$\underline{H}_3$), 0.86 (3H, s, POCH$_2$C(C$\underline{H}_3$)$_2$—) ppm $^{13}$C-NMR (CDCl$_3$; 100 MHz); δ 80.3 (dd, $^1J_{PC}$=179 Hz, $^2J_{PC}$=8 Hz, P$\underline{C}$(CH$_3$)$_2$OP), 77.7 (d, $^2J_{PC}$=7 Hz, PO$\underline{C}$H$_2$C(CH$_3$)$_2$—), 66.5 (d, $^2J_{PC}$=7 Hz, PO$\underline{C}$H$_2$CH$_2$CH$_2$CH$_3$), 32.5 (d, $J_{PC}$=6 Hz), 31.9 (d, $^3J_{PC}$=5 Hz, POCH$_2\underline{C}$(CH$_3$)$_2$—), 23.3, 21.7, 20.1, 18.6, 13.4 ppm element analysis and P % according to absorption analysis: C, 47.9%; H, 8.5%; P, 15.5%.

This application is related to Japanese application No. 2004-319528 filed on Nov. 2, 2004, whose priority is claimed and the disclosure of which is incorporated by reference in its entirety.

The invention claimed is:

1. A process for preparing a phosphonate, comprising the steps of:
subjecting a phosphite represented by the general formula (II):

(II)

wherein R$^1$ and R$^2$ are, the same as or different from each other, a straight or branched alkyl, cycloalkyl or aryl group; or alternatively R$^1$ and R$^2$, together with the oxygen atom and phosphorus atom to which they are attached, may constitute a ring structure and a carbonyl compound represented by the general formula (III):

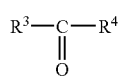

wherein R³ and R⁴ are, the same as or different from each other, a straight or branched alkyl or aryl group; or alternatively R³ and R⁴, together with the carbon atom to which they are attached, may constitute a ring structure to an addition reaction in the coexistence of 1 to 50 mol % of an aliphatic tertiary amine or a metallic amide with respect to the phosphite (II) and 0.1 to 5 mol % of a metallic halide with respect to the phosphite (II), to obtain a phosphonate having a tertiary alcoholic hydroxyl group represented by the general formula (I):

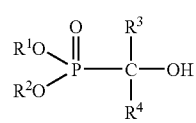

herein R¹, R², R³ and R⁴ each are as defined above.

2. The process for preparing a phosphonate of claim 1, wherein the aliphatic tertiary amine is triethylamine.

3. The process for preparing a phosphonate of claim 1, wherein the metallic halide is magnesium chloride.

4. The process for preparing a phosphonate of claim 1, wherein the phosphite (II) is selected among diethyl phosphite, di-n-propylphosphite, di-n-butylphosphite, di-n-octylphosphite, bis(2-ethylhexyl)phosphite, neopentylene phosphite and diphenylphosphite.

5. The process for preparing a phosphonate of claim 4, wherein the phosphite (II) is selected among di-n-butylphosphite, bis(2-ethylhexyl)phosphite and neopentylene phosphite.

6. The process for preparing a phosphonate of claim 1, wherein the numbers of carbon atoms contained in R³ and R⁴ of the carbonyl compound (III) each are 1 or more, and the sum of the numbers of carbon atoms contained in R³ and R⁴ is 2 to 12.

7. The process for preparing a phosphonate of claim 6, wherein the carbonyl compound (III) is selected among acetone, methyl ethyl ketone, methyl iso-butyl ketone, cyclohexane, acetophenone and benzophenone.

* * * * *